United States Patent
Jacob et al.

(10) Patent No.: US 11,141,128 B2
(45) Date of Patent: Oct. 12, 2021

(54) SYSTEMS AND METHODS FOR FOCAL SPOT MOTION DETECTION AND CORRECTION

(71) Applicant: General Electric Company, Schenectady, NY (US)

(72) Inventors: Biju Jacob, Niskayuna, NY (US); Mingye Wu, Glenville, NY (US); Mark Allen Adamak, Wauwatosa, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 102 days.

(21) Appl. No.: 16/714,291

(22) Filed: Dec. 13, 2019

(65) Prior Publication Data

US 2021/0177372 A1    Jun. 17, 2021

(51) Int. Cl.
*A61B 6/00* (2006.01)
*A61B 6/03* (2006.01)
*A61B 6/06* (2006.01)

(52) U.S. Cl.
CPC .............. *A61B 6/587* (2013.01); *A61B 6/032* (2013.01); *A61B 6/06* (2013.01); *A61B 6/585* (2013.01); *A61B 6/4476* (2013.01)

(58) Field of Classification Search
CPC .......... A61B 6/06; A61B 6/587; A61B 6/585; A61B 6/032; A61B 6/4476
See application file for complete search history.

(56) References Cited

U.S. PATENT DOCUMENTS

| | | |
|---|---|---|
| 5,065,420 A | 11/1991 | Levene |
| 6,175,609 B1 | 1/2001 | Edic et al. |
| 6,341,179 B1 | 1/2002 | Stoyle et al. |
| 7,266,179 B2 | 9/2007 | Deuringer et al. |
| 7,348,776 B1 | 3/2008 | Aksoy et al. |
| 8,249,213 B2 | 8/2012 | Noordhoek et al. |
| 10,779,778 B2 | 9/2020 | Rui et al. |
| 2006/0251210 A1* | 11/2006 | Chao .............. A61B 6/585 378/19 |
| 2012/0232385 A1 | 9/2012 | Kaori et al. |

(Continued)

FOREIGN PATENT DOCUMENTS

WO    2018208642 A1    11/2018

OTHER PUBLICATIONS

Fu, Lin, et al.; "Modeling and Estimation of Detector Response and Focal Spot Profil for High-Resolution Iterative CT Reconstruction", 2013 IEEE Nuclear Science Symposium and Medical Imaging Conference, Seoul, South Korea, pp. 1-5, Jun. 12, 2014.

(Continued)

*Primary Examiner* — Michael C Bryant
(74) *Attorney, Agent, or Firm* — Fletcher Yoder, P.C.

(57) ABSTRACT

The techniques disclosed may be used to detect and correct channel gain errors resulting from X-ray focal spot misalignment during the course of a scan. One benefit of the present invention relative to conventional techniques is that additional hardware is not required for detection of focal spot drift. Instead, the static mis-alignment of each blade is taken into account as part of estimating and correcting X-ray focal spot drift or mis-alignment. In this manner, the risk of image artefacts due to focal spot motion is reduced and the need for costly hardware solutions to detect focal spot motion is avoided.

21 Claims, 7 Drawing Sheets

(56) References Cited

U.S. PATENT DOCUMENTS

2012/0328076 A1* 12/2012 Ikhlef .................... G21K 1/025
378/62
2019/0008474 A1   1/2019 Martin et al.
2020/0222024 A1*  7/2020 Edie ...................... A61B 6/582

OTHER PUBLICATIONS

Ferrucci, Massimiliano, et al.; "Measurement of X-ray Computed Tomography Instrument Geometry by Minimization of Reprojection Errors—Implementation on Simulated Data", Precision Engineering, vol. 54, pp. 7-20, Oct. 2018.
European extended Search Report for EP Application No. 20210490.7 dated Apr. 26, 2021, 8 pages.

* cited by examiner

SYSTEMS AND METHODS FOR FOCAL SPOT MOTION DETECTION AND CORRECTION

BACKGROUND

Embodiments of the present specification relate generally to X-ray based imaging techniques, and more particularly to issues related to mis-alignment of an X-ray emission point and X-ray detector elements.

In an X-ray based imaging system, such as a computed tomography (CT) imaging system, an X-ray beam is emitted towards an object such as a patient or item (e.g., package, manufactured item, and so forth) to image a region of interest in the object. The beam is typically attenuated as it passes through the object. Subsequently, the attenuated beam is incident on a radiation detector having an array of detector elements. In response to the attenuated beam, the detector elements of the array generate respective electrical signals representative of internal information of the object. These electrical signals are processed by a data processing unit to generate an image representative of the region of interest in the object.

Reconstruction of images from the acquired data is generally based upon the assumption that X-ray photons have traveled in a straight path from an X-ray emission focal spot to the detector element at which the respective photon is detected. However, mis-alignment or movement of the X-ray focal spot with respect to one or more collimating elements or plates (e.g., a post-patient anti-scatter grid) may result in image artefacts that are detrimental to clinical use of imaging systems, such as CT imaging systems. This effect may be more significant in systems where the collimator blade pitch is larger than the channel (i.e., pixel) pitch, such that different channels may be effected to different degrees by the "shadow" case by the respective collimator blades.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a method is provided for estimating motion of an X-ray focal spot. In accordance with this method, image data is acquired by emitting X-rays from the X-ray focal spot toward a radiation detector comprising a plurality of channels. A first subset of the channels each have a collimator blade positioned above the respective channel and a second subset of channels are unobstructed by collimator blades. For at least one respective channel of the first subset: a relative channel gain is estimated for the respective channel; and X-ray focal spot motion is estimated using the relative channel gain and an X-ray focal spot motion sensitivity ratio for the respective channel.

In a further embodiment, an imaging system is provided. In accordance with this embodiment, the imaging system comprises: a source of X-ray radiation configured to emit X-rays from a focal spot during operation; a collimator comprising a plurality of collimator blades; a radiation detector, comprising a plurality of pixels, each pixel corresponding to a channel of the radiation detector. A first subset of the channels each have a collimator blade positioned above the respective channel and a second subset of channels are unobstructed by collimator blades. The imaging system further comprises: processing circuitry configured to perform acts comprising: acquiring image data by causing X-rays to be emitted from the X-ray source toward the radiation detector; for at least one respective channel of the first subset: estimating a relative channel gain for the respective channel; and estimating X-ray focal spot motion using the relative channel gain and an X-ray focal spot motion sensitivity ratio for the respective channel.

In an additional embodiment, a method is provided for correcting for focal spot motion. In accordance with this method, a relative channel gain is estimated for a respective channel of a radiation detector. Motion of an X-ray focal spot is estimated using the relative channel gain and an X-ray focal spot motion sensitivity ratio for the respective channel. A focal spot motion correction is calculated based on the estimate of motion of the X-ray focal spot. The focal spot motion correction factor is used as part of an image reconstruction or post-reconstruction process to correct or remove artifacts or other image irregularities.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
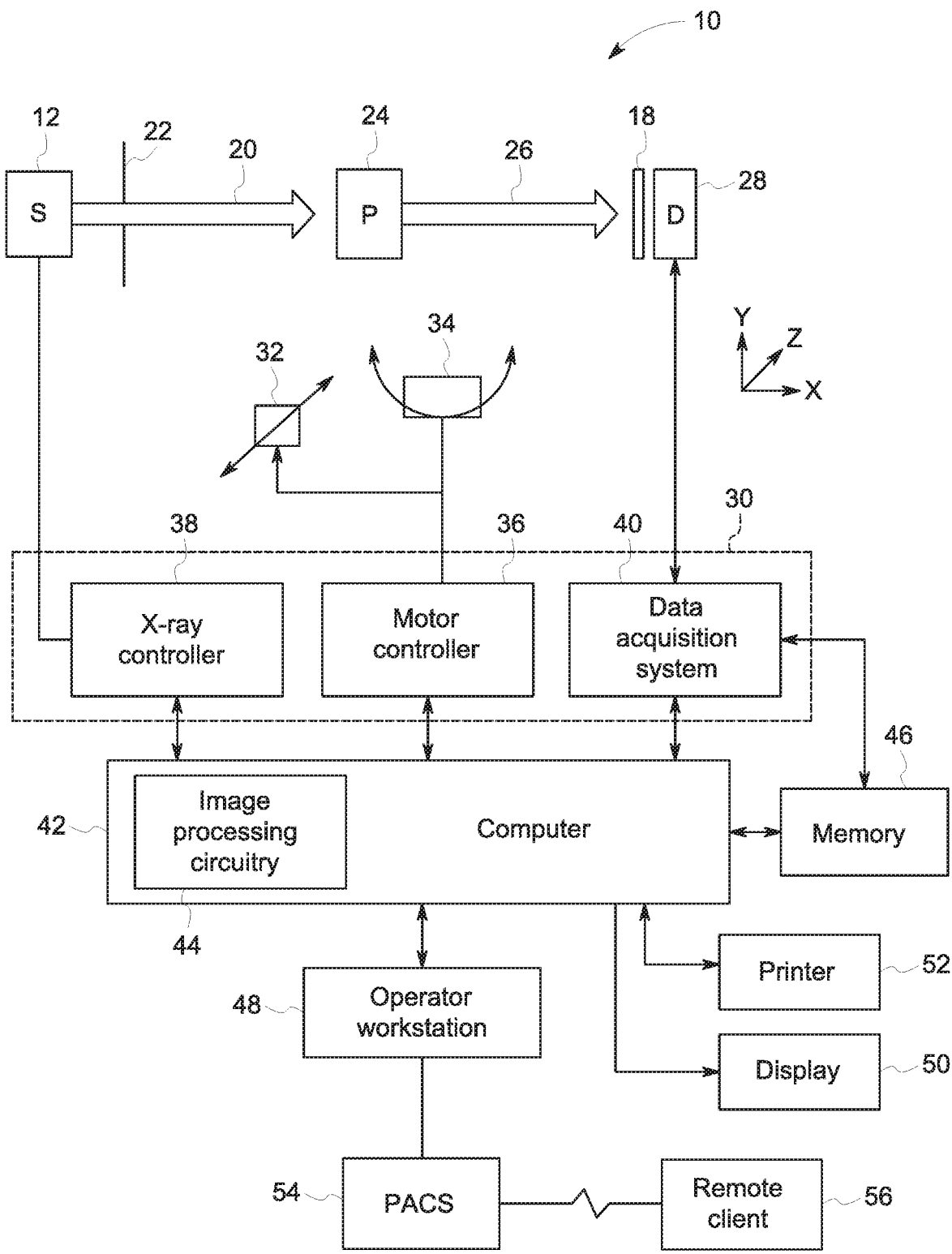
FIG. 1 depicts components of a computed tomography imaging system, in accordance with certain aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as tomographic image reconstruction for industrial Computed Tomography (CT) used in non-destructive inspection of manufactured parts or goods (i.e., quality control or quality review applications), and/or the non-invasive inspection of packages, boxes, luggage, and so forth (i.e., security or screening applications). In general, the present approaches may be useful in any imaging or screening context or image processing field mis-alignment of an X-ray emission point may be mis-aligned with an array of detector elements having associated anti-scatter or collimation elements (e.g., blades).

As discussed herein, reconstruction of images from the acquired X-ray transmission data is generally based upon the assumption that X-ray photons have traveled in a straight path from an X-ray emission focal spot to the detector element at which the respective photon is detected. However, mis-alignment or movement of the X-ray focal spot with respect to one or more collimating elements or plates (e.g., a post-patient anti-scatter grid) may result in image artefacts that are detrimental to clinical use of imaging systems, such as CT imaging systems. This effect may be more pronounced in systems where the collimator blade pitch is larger than the channel (i.e., pixel) pitch.

The techniques disclosed may be used to detect and correct channel gain errors resulting from X-ray focal spot mis-alignment during the course of a scan, which may result in the noted image artifacts. One benefit of the techniques described herein relative to conventional techniques is that they do not require additional hardware for detection of focal spot drift. Instead, the methods described herein take into account the static mis-alignment of each blade during manufacturing as part of estimating and correcting X-ray focal spot drift or mis-alignment. In this manner, the risk of image artefacts due to focal spot motion is reduced and the need for costly hardware solutions to detect focal spot motion is avoided.

With the preceding discussion in mind, FIG. 1 illustrates an embodiment of an imaging system 10 for acquiring and processing image data in accordance with structures and approaches discussed herein. In the illustrated embodiment, system 10 is a computed tomography (CT) system designed to acquire X-ray projection data and to reconstruct the projection data into volumetric reconstructions for display and analysis. The CT imaging system 10 includes one or more X-ray sources 12, such as one or more X-ray tubes or solid state emission structures which allow X-ray generation at one or more energy spectra during an imaging session.

In certain implementations, the source 12 may be positioned proximate to a pre-patient collimator and/or filter assembly 22 that may be used to steer the X-ray beam 20, to define the shape (such as by limiting off-angle emissions) and/or extent of a high-intensity region of the X-ray beam 20, to control or define the energy profile of the X-ray beam 20, and/or to otherwise limit X-ray exposure on those portions of the patient 24 not within a region of interest. In practice, the filter assembly or beam shaper 22 may be incorporated within the gantry, between the source 12 and the imaged volume.

The X-ray beam 20 passes into a region in which the subject (e.g., a patient 24) or object of interest (e.g., manufactured component, baggage, package, and so forth) is positioned. The subject attenuates at least a portion of the X-ray photons 20, resulting in attenuated X-ray photons 26 that impinge upon a pixelated detector array 28 formed by a plurality of detector elements (e.g., pixels) arranged in an m×n array. In the depicted example, the attenuated X-ray photons 26 pass through a collimator 18 (e.g., and ant-scatter grid) prior to reaching the detector array 28. As discussed herein, the collimator 18 may consist of a plurality of blades or other elements aligned substantially perpendicular to the surface of the detector array 28 and formed from an attenuating material that limit or prevent X-ray photons 26 traveling at off-angles (e.g., scattered X-rays) from reaching the detector array 28. The electrical signals reaching the detector array 28 are detected and processed to generate one or more projection datasets. In the depicted example, the detector 28 is coupled to the system controller 30, which commands acquisition of the digital signals generated by the detector 28.

A system controller 30 commands operation of the imaging system 10 to execute filtration, examination and/or calibration protocols, and may process the acquired data. With respect to the X-ray source 12, the system controller 30 furnishes power, focal spot location, control signals and so forth, for the X-ray examination sequences. In accordance with certain embodiments, the system controller 30 may control operation of the filter assembly 22, the CT gantry (or other structural support to which the X-ray source 12 and detector 28 are attached), and/or the translation and/or inclination of the patient support over the course of an examination.

In addition, the system controller 30, via a motor controller 36, may control operation of a linear positioning subsystem 32 and/or a rotational subsystem 34 used to move the subject 24 and/or components of the imaging system 10, respectively. For example, in a CT system, the radiation source 12 and detector 28 rotate about the object (e.g., patient 24) to acquire X-ray transmission data over a range of angular views. Thus, in a real-world implementation, the imaging system 10 is configured to generate X-ray transmission data corresponding to each of the plurality of angular positions (e.g., 360°, 180°+a fan beam angle (a), and so forth) covering an entire scanning area of interest.

The system controller 30 may include signal processing circuitry and associated memory circuitry. In such embodiments, the memory circuitry may store programs, routines, and/or encoded algorithms executed by the system controller 30 to operate the imaging system 10, including the X-ray source 12 and/or filter assembly 22, and to process the digital measurements acquired by the detector 28 in accordance with the steps and processes discussed herein. In one embodiment, the system controller 30 may be implemented as all or part of a processor-based system.

The source 12 may be controlled by an X-ray controller 38 contained within the system controller 30. The X-ray controller 38 may be configured to provide power, timing signals, and/or focal spot size and spot locations to the source 12. In addition, in some embodiments the X-ray controller 38 may be configured to selectively activate the source 12 such that tubes or emitters at different locations within the system 10 may be operated in synchrony with one another or independent of one another or to switch the source between different energy profiles during an imaging session.

The system controller 30 may include a data acquisition system (DAS) 40. The DAS 40 receives data collected by readout electronics of the detector 28, such as digital signals from the detector 28. The DAS 40 may then convert and/or process the data for subsequent processing by a processor-based system, such as a computer 42. In certain implementations discussed herein, circuitry within the detector 28 may convert analog signals of the detector to digital signals prior to transmission to the data acquisition system 40. The computer 42 may include or communicate with one or more non-transitory memory devices 46 that can store data processed by the computer 42, data to be processed by the computer 42, or instructions to be executed by image processing circuitry 44 of the computer 42. For example, a processor of the computer 42 may execute one or more sets of instructions stored on the memory 46, which may be a memory of the computer 42, a memory of the processor, firmware, or a similar instantiation. By way of example, the image processing circuitry 44 of the computer 42 may be configured to generate a diagnostic image. In one embodiment, the diagnostic image is a real-time image obtained using image reconstruction techniques applied to the plurality of signals obtained from the plurality of pixels 102 and corrected for X-ray focal spot motion or mis-alignment. In one embodiment, the diagnostic image is a CT image corrected for X-ray focal spot motion or mis-alignment and displayed on a display device 50 for assisting a medical practitioner.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data or images, and so forth. Additionally, the system 10 may include a printer 52 coupled to the operator workstation 48 and configured to print any desired measurement results. The display 50 and the printer 52 may also be connected to the computer 42 directly (as shown in FIG. 1) or via the operator workstation 48. Further, the operator workstation 48 may include or be coupled to a picture archiving and communications system (PACS) 54. PACS 54 may be coupled to a remote system or client 56, radiology department information system (RIS), hospital information system (HIS) or to an internal or external network, so that others at different locations can gain access to the image data.

Figure 2:
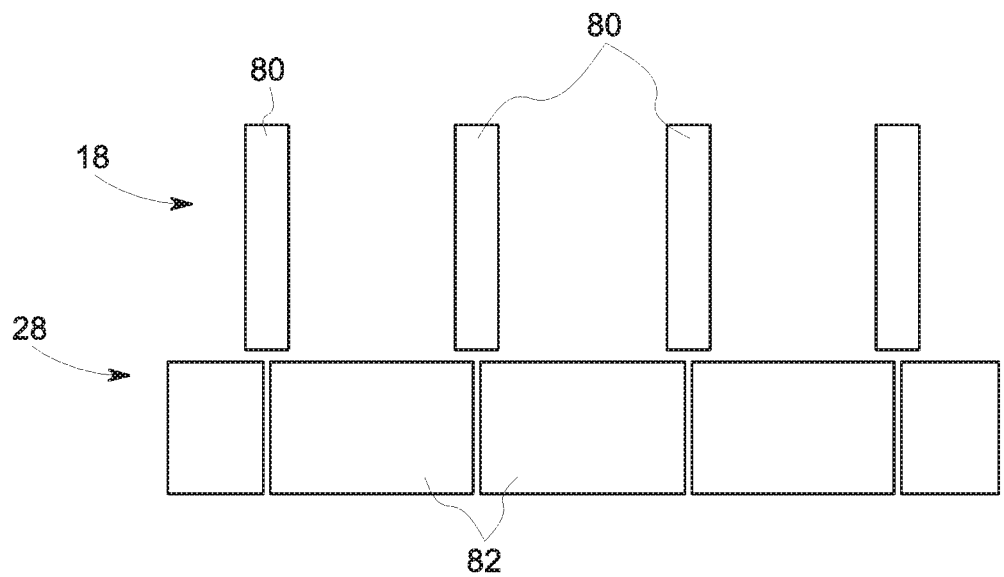
FIG. 2 depicts schematically a side-view of channels of a detector on which collimator blades are disposed, in accordance with certain aspects of the present disclosure.

With the preceding discussion of an overall imaging system 10 in mind, and turning to FIG. 2, an example of a prior detector 28 and collimator 18 arrangement is shown in a cut-away side view. In this example, the detector 28 is shown as including an array of pixels 82 each corresponding to a readout channel. In one such example, the pixel pitch may be approximately 1 mm. A set of collimator blades 80 are shown associated with the array of pixels 82 such that each pixel is separately collimated. The blades 80 are shown as being placed at where pixels are joined, such that shadowing attributable to the blades 80 is primarily at these joins, leaving the majority of the active area of the pixels 82 relatively free of shadows produced by the blades. In this manner, each pixel 82 is effected relatively consistently and uniformly by the collimator blades 80. In particular, if an X-ray emission focal spot is mis-aligned, the differential gain change attributable to the mis-alignment between adjacent channels is relatively small.

Figure 3:
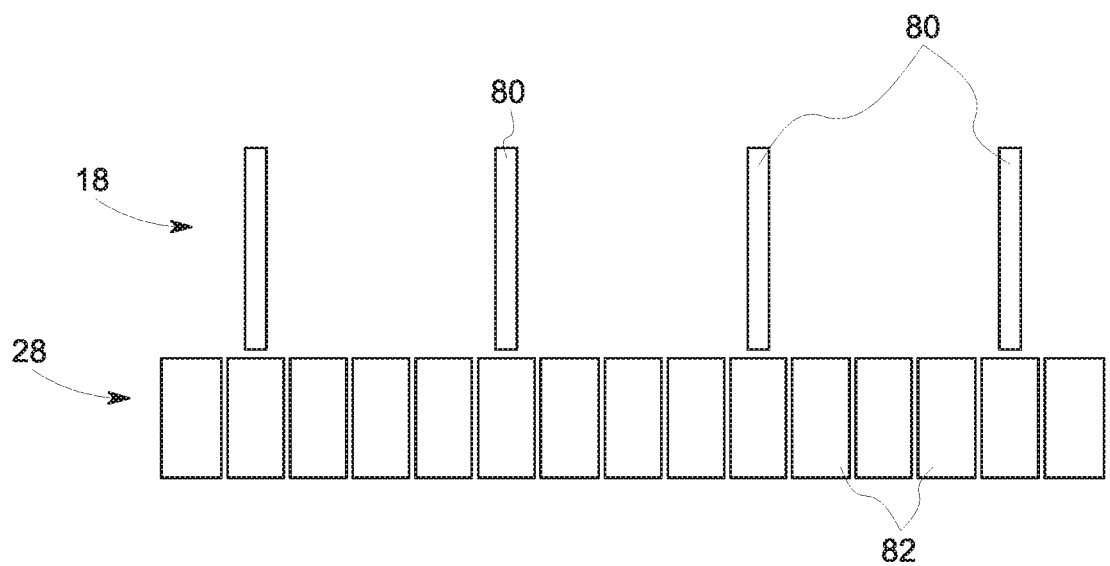
FIG. 3 depicts schematically an additional side-view of channels of a detector on which collimator blades are disposed, in accordance with certain aspects of the present disclosure.

Turning to FIG. 3, an example of a higher spatial resolution detector 28 having smaller pixels 82 (e.g., a pixel pitch less than 1 mm). Due to the smaller pixels, each channel may not be separated by respective collimator blades. Instead as shown, each collimator blade 80 may provide collimation for multiple pixels 82 (i.e., channels), with some pixels 82 touched by or immediately adjacent a blade 80 and others not adjacent a blade 80. Correspondingly, in the event of an X-ray focal spot mis-alignment the differential gain change due to X-ray focal spot mis-alignment between adjacent channels may be large due to the different placement of the relevant blade 80. That is, X-ray focal spot mis-alignment may result in large gain changes in high resolution detectors.

Figure 4:
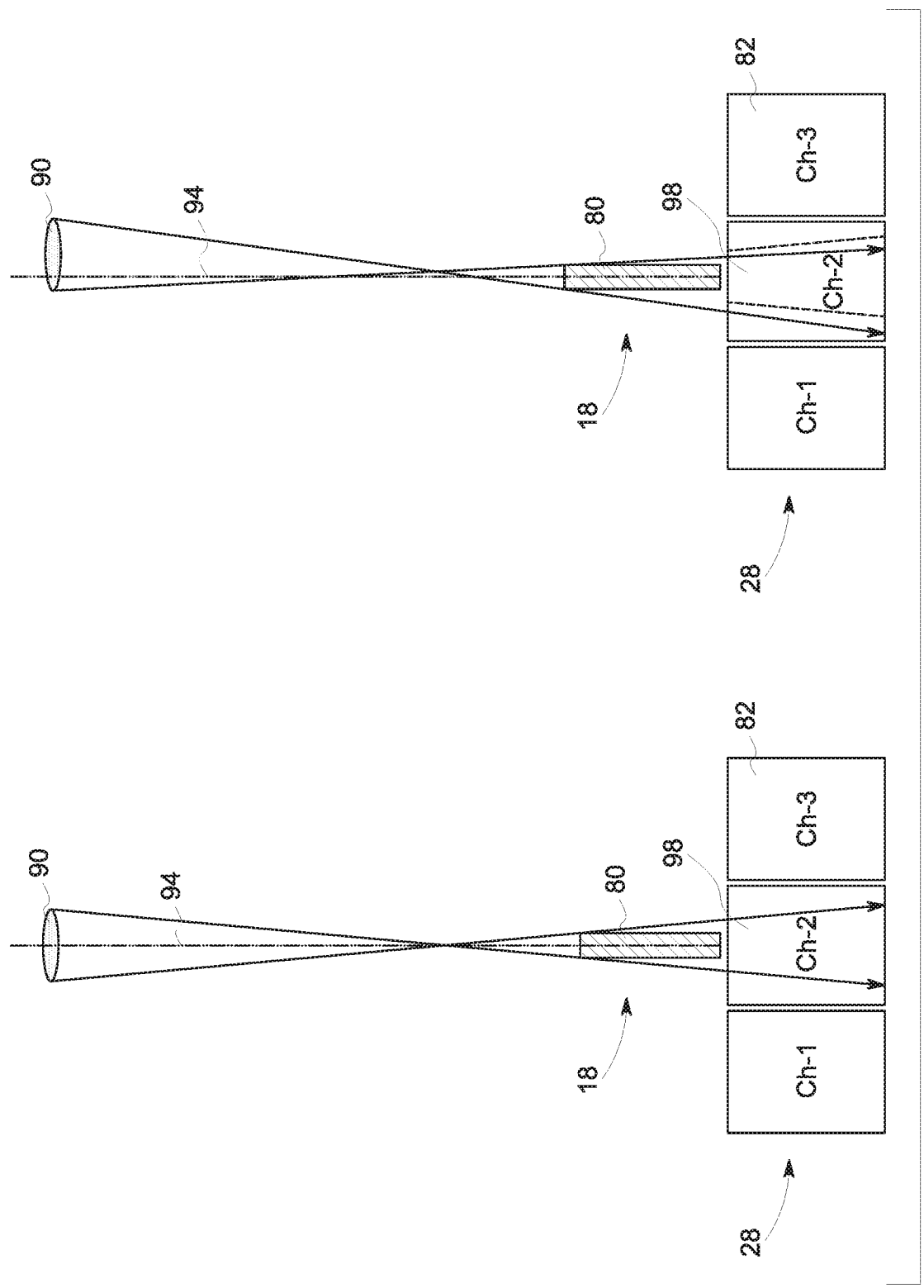
FIG. 4 visually illustrates an aligned and mis-aligned X-ray focal spot in the context of a collimated radiation detector, in accordance with certain aspects of the present disclosure.

Conceptually, this is illustrated on FIG. 4, where a side-by-side comparison of an aligned (left) and mis-aligned (right) X-ray focal spot 90 are illustrated in the context of a collimated detector 28. As shown in the left figure, when the X-ray focal spot 90 is aligned (as denoted by longitudinal axis 94 extending through the blade 80) with the blade 80, the shadow 98 cast by the blade is generally symmetric and minimized. Conversely, as shown on the right, when the X-ray focal spot 90 is misaligned with respect to the blade 80, the shadow 98 cast by the blade 80 is not symmetric with respect to different pixels 82 (denoted here as channels (CH) −1, −2, −3) and may be increased in size relative to when the X-ray focal spot 90 is aligned.

With the preceding discussion in mind, the mis-alignment of the collimator blade 80 and the X-ray focal spot 90 may result in image artifacts that are detrimental to clinical image quality. In particular, the effect of mis-alignment at the detector level is the introduction of small, but impactful changes in the gain of individual channels due to collimator blade shadowing of the X-ray focal spot, as shown in FIG. 4. That is, incremental change to the collimator blade shadow on the respective detector channels may lead to differential changes in channel gain, which can result in image artifacts. As illustrated with respect to FIGS. 2-4, this effect may be more significant in contexts where the pitch of the collimator blades 80 is greater that the pixel (i.e., channel) pitch such that there are pixels with a collimator blade above them and pixels without such a blade above them. If not detected and corrected, these changes due to X-ray focal spot mis-alignment may be wrongly interpreted as changes in object attenuation, thereby leading to image artifacts.

In practice, X-ray focal spot misalignment may be of two types. Static mis-alignment, as used herein, may be understood to be due to manufacturing tolerances, such as with respect to the deflection or tilt of collimator blades, and can be corrected to some extent by detector calibration. However, dynamic mis-alignment, may occur during the course of a scan due to thermal and mechanical forces generated during operation. Dynamic misalignment can be difficult to detect and, correspondingly, challenging to correct.

With the preceding in mind, the techniques discussed herein may be used to detect and correct channel gain errors attributable to X-ray focal spot misalignment during the course of a scan, including in higher resolution type system, as shown in FIG. 3. In particular, the techniques disclosed herein may be performed without additional hardware for the detection of X-ray focal spot drift.

By way of context, pixels 82 (i.e., channels) can be characterized as belonging into two groups: (1) pixels on which a collimator plate or blade 80 is present (denoted as pixels 82A herein) and pixels on which a collimator plate or blade 80 is not present (denoted as pixels 82B herein). It is those pixels 82A on which a collimator blade is present that are affected by X-ray focal spot misalignment (e.g., motion).

Figure 5:
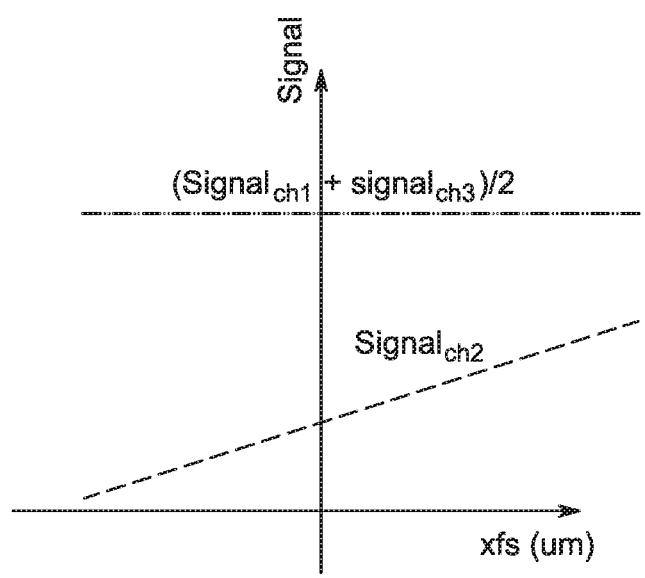
FIG. 5 graphically illustrates signal response of detector channels relative to X-ray focal spot position, in accordance with certain aspects of the present disclosure.

This is illustrated in the graph shown in FIG. 5 which characterizes X-ray focal spot motion in the context of the three-channel arrangement. As shown in FIG. 5, the signal seen at channel 2, on which the collimator blade 80 is positioned, varies based on X-ray focal spot (xfs) position. Conversely, the average signal seen at the flanking channels (i.e., channels 1 and 3), on which no collimator blade 80 is positioned, is uniform regardless of X-ray focal spot position. Each channel on which a collimator blade 80 is positioned can thus have its response (e.g., $r_{ch}$) characterized across a range of X-ray focal spot positions prior to installation and use, such as during post-manufacture calibration.

Figure 6:
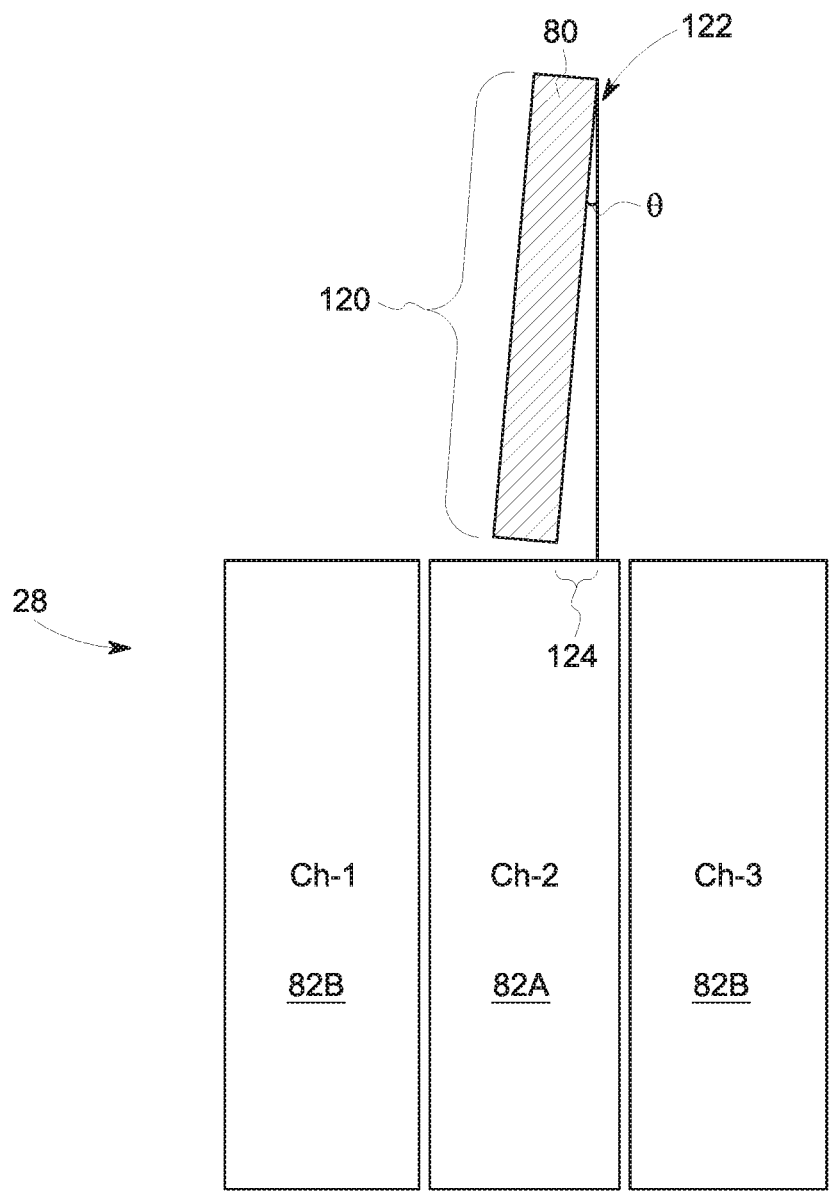
FIG. 6 depicts schematically a side-view of channels of a detector on which a tilted collimator blade is disposed and in conjunction with certain parameters of interest, in accordance with certain aspects of the present disclosure.

In addition, as noted herein, plate or blade 80 deflection that can result in artifacts as described herein can have both static and dynamic components. By way of example, static deflection of a blade 80 may be attributed to the manufacture of the blade 80 and does not change during operation or use. Dynamic deflection of a blade 80, conversely, may be attributed to movement or change in a blade 80 during a scan, such as due to thermal or mechanical forces. Effects of static deflections typically will be greater than those attributable to dynamic deflection. To illustrate these concepts, FIG. 6 depicts a deflected blade 80 of a collimator 18. In this example, the height of the blade or plate ($H_{blade}$) (denoted by reference number 120) is depicted along with an angle of deflection θ (denoted by reference number 122) and a blade deflection distance dx (denoted by reference number 124). Based on these observations, tilt of a collimator blade 80 can be modeled in accordance with:

$$\theta = \theta_{static} + \theta_{dynamic} \quad (1)$$

and $$dx = H_{blade} \sin(\theta) \quad (2)$$

With the preceding in mind, it may be observed that the relative sensitivity ($r_{ch}(\theta, xfs)$) of a given channel on which a blade 80 is positioned (i.e., a pixel 82A) with respect to neighboring pixels 82B is a function of the tilt or deflection of the respective blade 80. Thus, each channel having a blade 80 positioned over it (i.e., a pixel 82A) can be characterized by a sensitivity function relative to its neighbors, such as in accordance with:

$$r_{ch} = \frac{signal_{ch2}}{0.5 \cdot (signal_{ch1} + signal_{ch3})} \quad (3)$$

in the context of the present example and figures. Such characterization may be determined as part of a manufacturing or pre-installation calibration or assessment process.

Figure 7:
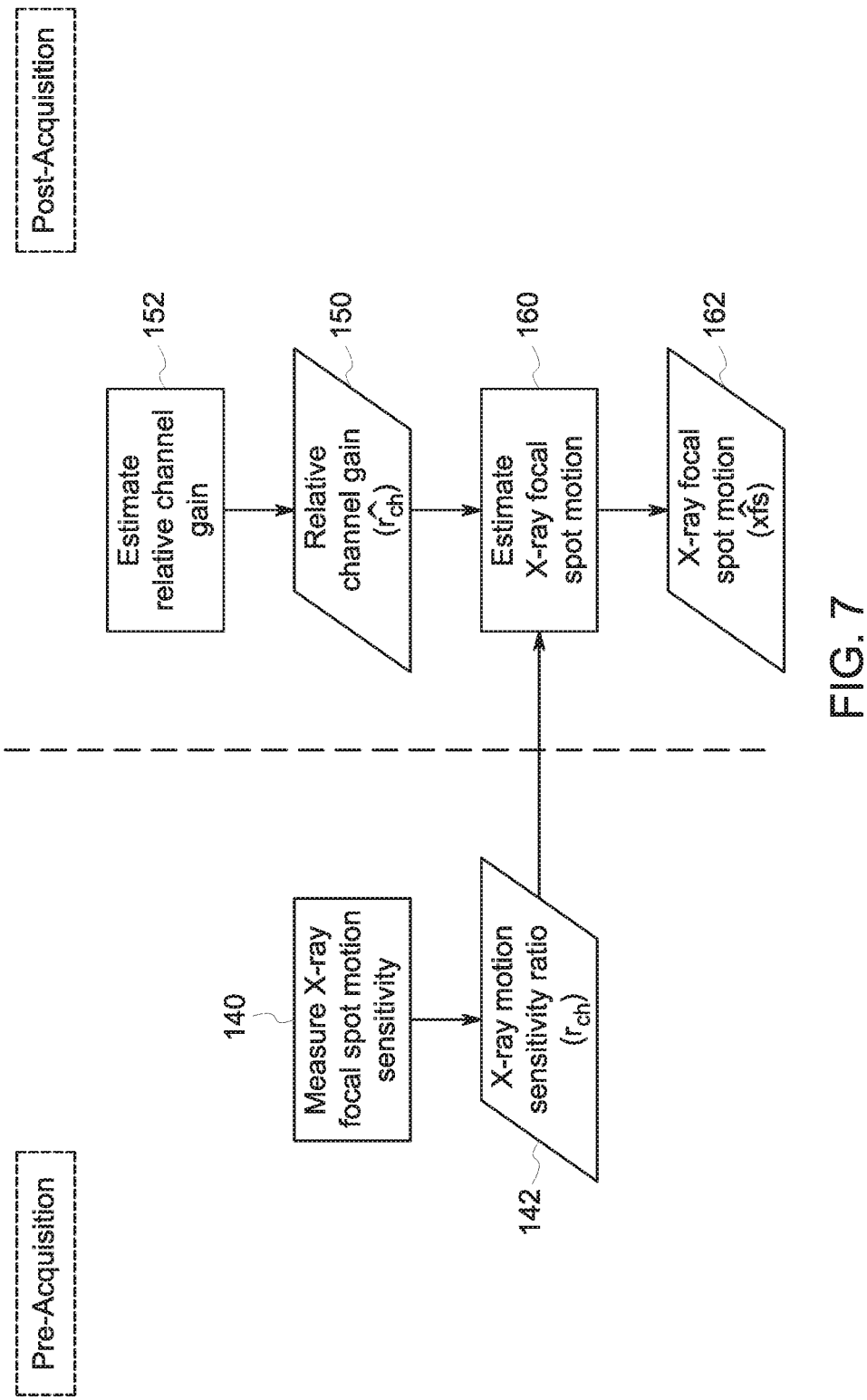
FIG. 7 depicts a process flow of one implementation of steps for estimating focal spot motion, in accordance with certain aspects of the present disclosure.

Turning to FIG. 7, a process flow of a method utilizing various aspects of these concepts to determine X-ray focal spot motion is provided. The implementation example described leverages the observation that neighboring channels that are unaffected by the X-ray focal spot motion can provide a constant baseline with which to compare those channels affected by the X-ray focal spot motion. Based on this observation, the sensitivity to static mis-alignment of each blade 80 is incorporated into the estimation and correction process via the measured focal spot motion sensitivity ratio.

In this process flow example, a given detector 28 and collimator 18 assembly may be calibrated or otherwise characterized to determine (step 140) X-ray focal spot motion sensitivity at each channel, which as noted above may be a function of collimator blade tilt. In the depicted example the X-ray focal spot motion sensitivity is characterized by an X-ray focal spot motion sensitivity ratio ($r_{ch}$) 142, as described in equation (3). This characterization may be done as part of the manufacture process of the detector/collimator assembly or at any other suitable time, such as during a pre-installation or other pre-use time period. Thus, this characterization of X-ray motion sensitivity may remain valid for the detector/collimator assembly for an extended period of use.

During use or operation (i.e., as part of acquiring clinical or diagnostic imaging data), relative channel gain ($\widehat{r_{ch}}$) 150 is estimated (step 152) post-acquisition. By way of example, post-acquisition relative channel gain ($\widehat{r_{ch}}$) may be estimated as:

$$\widehat{r_{ch}} = \frac{\sum_{Nslices} signal_{ch2}}{\sum_{Nslices} 0.5 * (signal_{ch1} + signal_{ch3})} \quad (4)$$

As shown in equation 4, the estimation of the relative channel gain 150 may be based on observations made over a number N image slices of acquired data, where N may be as few as one image slice or may be 5, 10, 30, 50, 100, or more image slices, depending on the examination acquisition protocol. In one implementation, the relative channel gain 150 may be represented as a probabilistic distribution (characterized by measures of central tendency such as a mean, median, and mode, as well as an associated variance) corresponding to ratios observed for different respective N image slices. Once the post-acquisition relative channel gain ($\widehat{r_{ch}}$) 150 is determined, it may be used in conjunction with the known X-ray focal spot motion sensitivity 142 to statistically estimate (step 160) X-ray focal spot motion ($\widehat{xfs}$) 162 during the image data acquisition. That is, X-ray focal spot motion in one such embodiment is based on determining a suitable subset of channels in a given acquisition that are unobstructed by collimator blades and exhibit minimal differential gain sensitivity in response to motion of the X-ray focal spot.

Figure 8:
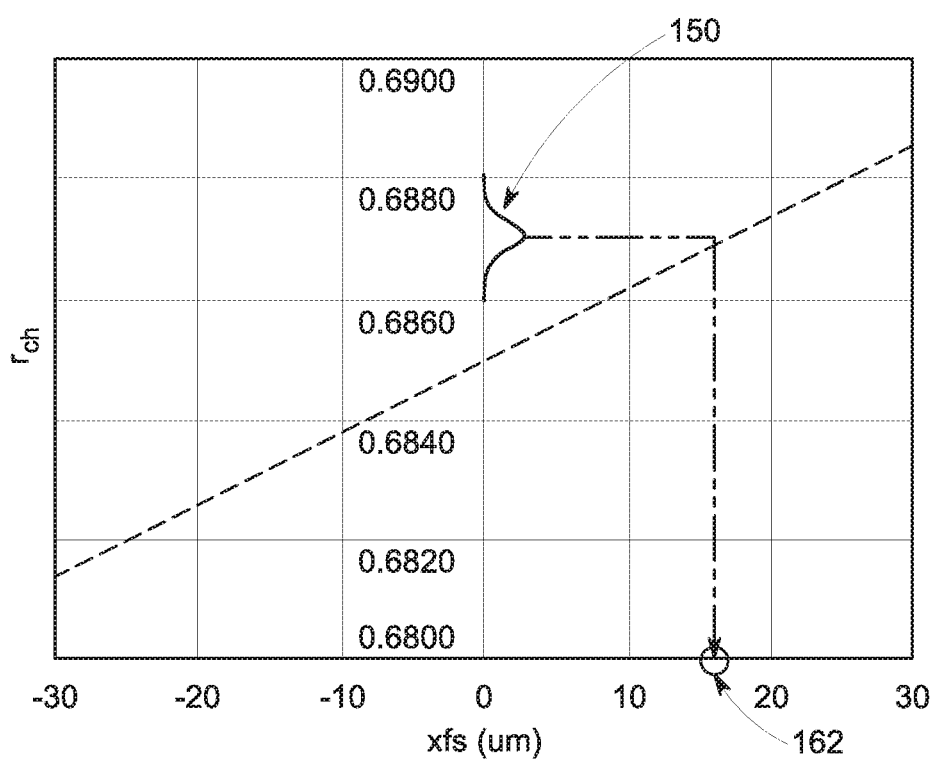
FIG. 8 graphically illustrates use of a relative channel gain to determine X-ray focal spot position, in accordance with certain aspects of the present disclosure.

An example of this is graphically illustrated on FIG. 8. In this example, the estimation of ($\widehat{r_{ch}}$) 150, here depicted probabilistically as a distribution, may be mapped to the vertical axis corresponding to $r_{ch}$, which may derived or determined from the X-ray focal spot motion sensitivity determined as step 140. In the depicted example, $\widehat{r_{ch}}$ 150 may be used with the known X-ray focal spot motion sensitivity for the channel in question to estimate the position or motion of the X-ray focal spot $\widehat{xfs}$ 162 plotted horizontally in FIG. 8, during the image data acquisition.

The X-ray focal spot motion $\bar{x}\bar{f}s$ 162 estimated at the respective channel(s) during the image data acquisition may then be used to correct for or otherwise address any observed X-ray focal spot motion, such as by calculating a focal spot motion correction factor(s) used as part of the image reconstruction or post-reconstruction processes, to correct or remove artifacts or other image irregularities. By way of example, in certain embodiments signal correction may be limited to those channels associated with a pixel on which a plate 80 is positioned, i.e., those channels where signal change may be due to misalignment of the blades 80. Similarly, to avoid signal corruption due to scatter and/or noise, measurements and corrections may be averaged over multiple view and/or for multiple plates.

Technical effects of the invention include a CT imaging system capable of reducing the effects of X-ray focal spot motion during an imaging operation, such as by reducing or eliminating image artifacts attributable to X-ray focal spot motion. Estimation and/or correction of X-ray focal spot motion effects are achieved without additional hardware.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for estimating motion of an X-ray focal spot, comprising the acts of:
   acquiring image data by emitting X-rays from the X-ray focal spot toward a radiation detector comprising a plurality of channels, wherein a first subset of the channels each have a collimator blade positioned above the respective channel and a second subset of channels are unobstructed by collimator blades;
   for at least one respective channel of the first subset:
      estimating a relative channel gain for the respective channel; and
      estimating X-ray focal spot motion using the relative channel gain and an X-ray focal spot motion sensitivity ratio for the respective channel.

2. The method of claim 1, wherein the X-ray focal spot motion sensitivity ratio is determined as part of a pre-installation calibration of the radiation detector.

3. The method of claim 1, wherein channels of the first subset exhibit non-uniform differential gain sensitivity in response to motion of the X-ray focal spot.

4. The method of claim 1, wherein channels of the second subset exhibit minimal differential gain sensitivity in response to motion of the X-ray focal spot.

5. The method of claim 1, wherein the X-ray focal spot motion sensitivity ratio for the respective channel comprises a ratio of signal measured at the respective channel over an average of signal measured at adjacent channels that are in the second subset.

6. The method of claim 1, wherein the relative channel gain for the respective channel comprises a ratio of a summed signal measured at the respective channel for N image slices over, for the N image slices, a summed average of signal measured at adjacent channels that are in the second subset.

7. The method of claim 1, wherein the relative channel gain for the respective channel is represented as a probabilistic distribution.

8. The method of claim 1, wherein estimating X-ray focal spot motion comprises determining a suitable subset of channels in a given acquisition that belong to the second subset of channels and exhibit minimal differential gain sensitivity in response to motion of the X-ray focal spot.

9. The method of claim 1, wherein estimating X-ray focal spot motion comprises associating the relative channel gain for the respective channel with a representation of the X-ray focal spot motion sensitivity plotted again X-ray focal spot location.

10. The method of claim 1, further comprising:
    calculating a focal spot motion correction based on the estimate of X-ray focal spot motion; and
    using the focal spot motion correction as part of an image reconstruction or post-reconstruction process to correct or remove artifacts or other image irregularities.

11. An imaging system, comprising:
    a source of X-ray radiation configured to emit X-rays from a focal spot during operation;
    a collimator comprising a plurality of collimator blades;
    a radiation detector, comprising a plurality of pixels, each pixel corresponding to a channel of the radiation detector, wherein a first subset of the channels each have a collimator blade positioned above the respective channel and a second subset of channels are unobstructed by collimator blades;
    processing circuitry configured to perform acts comprising:
       acquiring image data by causing X-rays to be emitted from the X-ray source toward the radiation detector;
       for at least one respective channel of the first subset:
          estimating a relative channel gain for the respective channel; and
          estimating X-ray focal spot motion using the relative channel gain and an X-ray focal spot motion sensitivity ratio for the respective channel.

12. The imaging system of claim 11, wherein channels of the first subset exhibit non-uniform differential gain sensitivity in response to motion of the X-ray focal spot.

13. The imaging system of claim 11, wherein channels of the second subset exhibit uniform differential gain sensitivity in response to motion of the X-ray focal spot.

14. The imaging system of claim 11, wherein the X-ray focal spot motion sensitivity ratio for the respective channel comprises a ratio of signal measured at the respective channel over an average of signal measured at adjacent channels that are in the second sub set.

15. The imaging system of claim 11, wherein the relative channel gain for the respective channel comprises a ratio of a summed signal measured at the respective channel for N image slices over, for the N image slices, a summed average of signal measured at adjacent channels that are in the second subset.

16. The imaging system of claim 11, wherein estimating X-ray focal spot motion comprises associating the relative channel gain for the respective channel with a representation of the X-ray focal spot motion sensitivity plotted again X-ray focal spot location.

17. The imaging system of claim 11, wherein the processing circuitry is further configured to perform acts comprising:
    calculating a focal spot motion correction based on the estimate of X-ray focal spot motion; and using the focal spot motion correction as part of an image reconstruction or post-reconstruction process to correct or remove artifacts or other image irregularities.

18. A method for correcting for focal spot motion, comprising the acts of:
estimating a relative channel gain for a respective channel of a radiation detector;
estimating motion of an X-ray focal spot using the relative channel gain and an X-ray focal spot motion sensitivity ratio for the respective channel;
calculating a focal spot motion correction based on the estimate of motion of the X-ray focal spot; and
using the focal spot motion correction factor as part of an image reconstruction or post-reconstruction process to correct or remove artifacts or other image irregularities.

19. The method of claim 18, wherein the respective channel has a collimator blade positioned between a pixel of the respective channel and an X-ray source comprising the X-ray focal spot.

20. The method of claim 18, the respective channel exhibits non-uniform differential gain sensitivity in response to the motion of the X-ray focal spot.

21. The method of claim 18, wherein the relative channel gain for the respective channel comprises a ratio of a summed signal measured at the respective channel for N image slices over, for the N image slices, a summed average of signal measured at adjacent channels.

* * * * *